United States Patent [19]

McLean, Sr.

[11] 4,073,887
[45] Feb. 14, 1978

[54] COMPOSITION FOR TREATING INGROWN TOENAILS
[75] Inventor: Ellis J. McLean, Sr., Moultrie, Ga.
[73] Assignee: Edward Price McLean, Sr., Moultrie, Ga.
[21] Appl. No.: 495,531
[22] Filed: Aug. 7, 1974

Related U.S. Application Data

[63] Continuation-in-part of Ser. No. 331,094, Feb. 9, 1973, abandoned.
[51] Int. Cl.² ............................................. A61K 33/26
[52] U.S. Cl. .................................... 424/147; 424/61; 424/65
[58] Field of Search ........................... 424/61, 65, 147
[56] References Cited
PUBLICATIONS
Stille, Nat. Disp., Lea Bros., Phila., 5th Ed., 1896, pp. 109, 110, 169, 172, 742, 748, 749.
Conn, Current Therapy, W. B. Saunders Co., Phila., 1963, p. 455.
Outgro, Trademark No. 275149, label received May 14, 1970, p. 1.
Drill, Pharm. in Med., McGraw-Hill, N.Y., 1954, pp. 45, 15-16.

Primary Examiner—Albert T. Meyers
Assistant Examiner—Anna P. Fagelson
Attorney, Agent, or Firm—Cushman, Darby & Cushman

[57] ABSTRACT

Onyxis or ingrowing of the nails and especially onychocryptosis, unguis incarnatus, or ingrowing of the toenails is treated by applying to the affected nail and adjacent cuticle and skin area a topical solution comprising, as the active ingredient, ferric subsulfate solution, and allowing the solution to remain in contact with the nail and the surrounding skin area, by repeating this application night and morning for several days, until the unguis incarnatus is significantly alleviated.

5 Claims, No Drawings

COMPOSITION FOR TREATING INGROWN TOENAILS

CROSS REFERENCE TO RELATED APPLICATION

This is a continuation-in-part of my earlier application, Ser. No. 331,094 filed Feb. 9, 1973 now abandoned.

BACKGROUND OF THE INVENTION

This application relates to the treatment of ingrowing nails, especially ingrowing toenails, and includes a method of treating this especially painful and troublesome condition using a topically applied pharmaceutical composition.

Ingrowing nail or unguis incarnatus, especially ingrowing toenail, a frequent nail malady, occurs chiefly on the great toes where there occurs an "abnormal" nail growth into the nail fold, leading to a painful and inflammatory condition. In some cases the edge of the nail apparently acts as a foreign body and often results in extreme pain and (possibly) granulation of the affected tissue. The condition may be caused by wearing improperly fitting shoes, by improper trimming of the toenail, or by a physical pressure which might occur to the nail through an accident or other similar conditions. It is believed that the above conditions generally create the beginning of the affliction of an ingrowing toenail; however, the specific cause may be due to one or several conditions, many of which are unknown.

The most widely accepted method for relief of this problem is the surgical removal of the entire nail to relieve the pressure. In some instances, the surgical procedure of removing the overhanging lateral nail fold is used, that is, removing the affected tissue adjacent to the affected nail. Under the latter method, the nail itself is not altered or removed. This procedure is described in Andrews' Diseases of the Skin, 6th Ed., p. 878.

DETAILED DESCRIPTION OF THE INVENTION

I have now discovered a simple, safe, convenient and expedient method of treating ingrowing toenails that may be carried out by a person suffering therefrom by using a topical application which contains, as the essential active ingredient, ferric subsulfate solution. This ferric subsulfate solution is also known as Monsel's solution, a widely recognized and accepted preparation that has, in the past, been used externally for its styptic properties and also as an astringent in a variety of minor skin disorders. This preparation has been recognized as useful for stopping surface bleeding of cuts, wounds, etc., on the skin of humans (reference: Remington's Practice of Pharmacy, 9th Ed., pp. 431–432).

In the following description, nails or onyx will be referred to in its general sense as including both fingernails and toenails. Similarly, the term onyxis is general to nails, whereas the term onychocryptosis is specific to ingrowing of the toenail. As ingrowing toenails are more prevalent in the adult population and often more troublesome than ingrowing fingernails, the following discussion will be cast in terms of toenails; it will be understood, however, that both toenails and fingernails are susceptible to treatment according to my research, experiments and discoveries.

Ferric subsulfate solution is an aqueous solution containing, in each 100 cc., basic ferric sulfate [approximately $Fe_4(OH)_2(SO_4)_5$], equivalent to not less than 20 Gm. and not more than 22 Gm. of Fe.

Ferric subsulfate solution is also known as Monsel's Solution; it has a reddish-brown color, is nearly odorless, has an acid pH, an astringent taste, and is miscible with water. Ferric subsulfate solution N.F. is probably the most valuable official styptic solution. It is less irritating than ferric sulfate owing to the smaller proportion of sulphuric acid. This preparation additionally is used for minor skin disorders and is described as practically non-toxic in Remington's Practice of Pharmacy, 9th Ed., pp. 431–432 and the Merck Index, 8th Ed., pp. 453–454.

It is recognized that possibly minor variations in the chemical formulation of ferric subsulfate solution might be used and slightly altered in its chemical or physical characteristics in order that the advantages of ferric subsulfate solution might be compounded in a different form and therefore be useful in the same manner as my invention as described. For the purpose of this application, and for convenience, I prefer to use the aqueous ferric subsulfate solution (Monsel's Solution) only, which is available commercially from several manufacturers, and, which is prepared according to the description as given in the United States Pharmacopea, 25th Ed., p. 574, and/or prepared as described in Remington's Practice of Pharmacy, 9th Ed., pp. 431–432, referred to on Lines 13–15 on page 2. This solution, prepared in this manner, conforms to National Formulary XI specifications. Ferric subsulfate solution is no longer "official", in that it is not included in the current edition of the National Formulary. This is perhaps due to the fact that no real and useful application for ferric subsulfate solution has previously been found or discovered other than its value for styptic purposes and for minor skin disorders as referred to by Remington.

Ferric subsulfate solution is typically evaluated in terms of the iron content. When prepared according to the procedure described in Example 1 (page 9, lines 1–42), as quoted from Remington's Practice of Pharmacy, 9th Ed., p. 431, the finished product will contain not less than 20 Gm. and not more than 22 Gm. of Fe per 100 cc. of the solution. This will also conform to N.F. XI standards.

The aqueous solution of ferric subsulfate, as described, may be conveniently packaged in small one or two ounce amber glass containers. The solution may also be easily applied using a small cotton swab.

Certain procedures preliminary to the application of the ferric subsulfate solution are desirable but success has been obtained in all cases without this preliminary procedure. It is recommended that the patient suffering from the effects of an ingrowing toenail should soak the foot on which the affected nail is located in hot water as warm as it is comfortable for the patient to withstand. The hot water should include an adequate amount of a mild toilet soap in order to accomplish the removal of any extraneous matter or epidermis tissue that might exist but, more importantly, the soaking for a period of from five to ten minutes in the hot water and the use of the toilet soap is recommended primarily for the purpose of permitting the natural skin oil to be removed from the skin and toes. After soaking, the foot should be thoroughly rinsed and dried with a soft cloth. Following this preliminary procedure, the ferric subsulfate solution is applied as follows: Immerse a cotton swab into the ferric subsulfate solution liquid and then, using the swab, apply this preparation to the perimeter of the affected nail, also to the cuticle and the skin adjacent to the nail. Finally, if the nail is not too painful, an application of this preparation, using the swab, should, where possible, be pressed under the edges of the nail.

The above procedure of application should be followed twice a day and, for convenience, this may be in the morning and at night before retiring. This treatment should be continued for a period of time until symptomatic relief from the ingrowing toenail is achieved. The duration of treatment will vary from case to case. However, good results have been obtained in a period as short as two days. In some instances, a week or even ten days treatment may be required to produce significant relief of the ingrowing toenail symptoms. The manner in which the ferric subsulfate solution, when used as described above, produces relief and eliminates the infections that often accompany such maladies of ingrowing toenails has not at this time been clearly established. In any event, this ferric subsulfate solution, applied topically as described, does exhibit unusual antiseptic properties as it reduces the soreness and infections that frequently are symptomatic of ingrowing toenails. This relief of soreness and the relief of the infections usually takes place within 24 to 48 hours. It is recommended that the treatment be followed until all symptoms stemming from the ingrowing nail are eliminated. During treatment, the patient may notice a slight yellowish-brown coloration to the surrounding skin and possibly the nail edge. This has not resulted in any problems, as the solution itself is a reddish, dark brown liquid and the discoloration will disappear within a few days following completion of the treatment.

The following examples will serve to further illustrate my invention and discovery.

EXAMPLE 1

Preparation of Ferric Subsulfate Solution

"FERRIC SUBSULFATE SOLUTION N. F. Liquor Ferri Subsulfatis (Liq. Ferr. Subsulf. - Monsel's Solution, Basic Ferric Sulfate Solution, Sp. Solucion de Subsulfato de Hierro)

Ferric Subsulfate Solution is an aqueous solution containing, in each 100 cc., basic ferric sulfate [approximately $Fe_4(OH)_2(SO_4)_5$], equivalent to not less than 20 Gm. and not more than 22 Gm. of Fe.

|  | Metric | Alternative |
|---|---|---|
| Ferrous Sulfate | 1045 Gm. | 34 oz. av. 387 gr. |
| Sulfuric Acid | 55 cc. | 1 fl. oz. 365 min. |
| Nitric Acid |  |  |
| Distilled Water, each, a sufficient quantity, |  |  |
| To make | 1000 cc. | 2 pints |

Add the sulfuric acid to 800 cc. (25 fl. oz. 288 min.) of distilled water in a capacious porcelain dish, and heat the mixture nearly to 100° C.; then add 75 cc. (2 fl. oz. 192 min.) of nitric acid, and mix well. Divide the ferrous sulfate, coarsely powdered, into four approximately equal portions, and add these portions one at a time to the hot liquid, stirring after each addition until effervescence ceases. If, after the ferrous sulfate has dissolved, the solution is of a black color, add nitric acid, a few drops at a time, with heating and stirring, until red fumes cease to be evolved. Boil the solution until it assumes a red color and is free from nitric acid, as indicated by the test below, maintaining the volume at about 1000 cc. (2 pints) by the addition of distilled water as needed. Cool, and add enough distilled water to make the product measure 1000 cc. (2 pints); filter, if necessary until the product is clear.

Note: Crystallization may take place in the Solution at low temperatures, but the crystals will redissolve upon warming the solution."

EXAMPLE 2

Treatment of Ingrowing Toenails

A mature male patient suffering from the symptoms of an ingrowing toenail was treated by first soaking the foot and the affected toenail in a basin containing about two quarts of reasonably hot water and the toenail area was cleansed with a mild hand soap to remove natural skin oils and tissue debris. After soaking for about 5 to 10 minutes, the foot was removed from the water and thoroughly dried. The solution of Example 1 was applied topically using a cotton swab to the edges of the affected toenail, the cuticle and the adjacent skin area. The cotton swab was again immersed in this preparation and as much of the liquid as possible was forced under the edge of the affected nail. The application was then allowed to dry, which normally requires approximately 5 to 7 minutes. It is important that the patient allow the solution to dry completely since the iron content would possibly stain the socks, hose, bed linens, or any other similar material.

The same treatment of applying the solution was repeated the following morning and the following evening of the same day; further, the twice a day treatment was repeated for a total of 5 days, or ten applications of the solution of Example 1. After 5 days all symptoms of the ingrowing toenail were alleviated. However, the healing process began within 48 hours from the initial use of this preparation.

EXAMPLE 3

Treatment of Ingrowing Toenails

An adult male suffering from two ingrowing toenails was treated with the solution of Example 1 using the procedure described in Example 2 morning and night. At the end of three days of treatment the symptoms were completely relieved on both toenails.

What is claimed is:

1. A process for treating unguis incarnatus comprising the steps of:
   (a) applying to the nail and the skin area adjacent thereto of a person suffering from unguis incarnatus, a topical composition consisting essentially of ferric subsulfate solution;
   (b) maintaining said ferric subsulfate in contact with the affected onyx and skin area adjacent thereto for several hours; and
   (c) repeating steps (a) and (b) at least once daily for several days until the symptoms of said unguis incarnatus are substantially alleviated.

2. The process as claimed in claim 1, wherein steps (a) and (b) are repeated twice daily for a period not exceeding about 10 days.

3. A process for treating ingrowing toenails comprising the sequential steps of:
   (a) soaking the foot of the person suffering from ingrowing toenails on which the affected nail is located in hot, soapy water for a period of from about 5 to about 10 minutes;
   (b) rinsing and drying the foot;

(c) applying to the affected toenail and adjacent cuticle and surrounding skin area ferric subsulfate solution;

(d) repeating steps (a) through (c), inclusive, for several days, at least once a day, until the ingrowing toenail symptoms are substantially alleviated.

4. The process as claimed in claim 3, wherein the ferric subsulfate solution is applied under the edges of the affected nail.

5. The process as claimed in claim 3, wherein steps (a) through (c) inclusive, are repeated twice daily for a period not exceeding about 10 days.

* * * * *